US009539420B2

(12) United States Patent
Tan

(10) Patent No.: US 9,539,420 B2
(45) Date of Patent: Jan. 10, 2017

(54) MULTI-PATH CONTROL VALVE

(71) Applicant: Ta-lun Tan, Taipei (TW)

(72) Inventor: Ta-lun Tan, Taipei (TW)

( * ) Notice: Subject to any disclaimer, the term of this patent is extended or adjusted under 35 U.S.C. 154(b) by 94 days.

(21) Appl. No.: 14/495,060

(22) Filed: Sep. 24, 2014

(65) Prior Publication Data

US 2015/0088055 A1    Mar. 26, 2015

(30) Foreign Application Priority Data

Sep. 24, 2013   (TW) .............................. 102217815 U

(51) Int. Cl.
| | |
|---|---|
| *F16K 7/02* | (2006.01) |
| *A61M 39/22* | (2006.01) |
| *F16K 31/54* | (2006.01) |
| *F16K 7/06* | (2006.01) |
| *F16K 11/02* | (2006.01) |
| *A61M 1/36* | (2006.01) |

(52) U.S. Cl.
CPC ........... *A61M 39/223* (2013.01); *A61M 1/367* (2013.01); *A61M 1/3659* (2014.02); *A61M 1/3661* (2014.02); *F16K 7/06* (2013.01); *F16K 11/027* (2013.01); *F16K 31/54* (2013.01); *A61M 2039/224* (2013.01)

(58) Field of Classification Search
USPC .......................................................... 251/7
See application file for complete search history.

(56) References Cited

U.S. PATENT DOCUMENTS

| | | | |
|---|---|---|---|
| 3,411,534 A | | 11/1968 | Rose |
| 4,491,156 A | * | 1/1985 | Lee, II ................... F16K 7/045 137/595 |
| 4,691,738 A | * | 9/1987 | McCune ............ A61B 17/1355 137/595 |
| 4,821,996 A | * | 4/1989 | Bellotti ................. F16K 11/027 251/230 |
| 5,188,334 A | * | 2/1993 | Yoshii ..................... F16K 7/045 137/316 |
| 5,573,223 A | * | 11/1996 | Kawabe ................ F16K 11/027 251/4 |
| 5,901,745 A | * | 5/1999 | Buchtel .................... F16K 7/06 137/595 |
| 6,079,691 A | * | 6/2000 | Dragone ............... F16K 11/027 251/4 |
| 2009/0112164 A1 | | 4/2009 | Reilly et al. |
| 2010/0064900 A1 | | 3/2010 | Reyhanloo |

FOREIGN PATENT DOCUMENTS

FR           2622666 A1     5/1989

OTHER PUBLICATIONS

Extended European Search Report issued in corresponding European Application No. 14186166.6 dated Mar. 10, 2015 (6 pages).
Office Action issued in corresponding European Application No. 14186166.6 dated Mar. 17, 2016 (5 pages).

* cited by examiner

*Primary Examiner* — John Fox
(74) *Attorney, Agent, or Firm* — Osha Liang LLP

(57) ABSTRACT

A control valve includes a tube housing, a tube within the tube housing, and a clamp within the tube housing. The tube is disposed between a first portion of the tube housing and the clamp, and the clamp is movable between an open position and a closed position. The clamp in the open position is located away from the first portion of the tube housing, and the clamp in the first closed position is located adjacent to the first portion of the tube housing.

6 Claims, 3 Drawing Sheets

MULTI-PATH CONTROL VALVE

CROSS-REFERENCE TO RELATED APPLICATIONS

The present application claims the benefit of priority to TW Utility Model Application No. 102217815, filed on Sep. 24, 2013 which is hereby incorporated by reference in its entirety herein.

BACKGROUND

Description of Related Art

A multi-path valve system may be used to control a fluid flow path within a system having a plurality of tubes, by controlling the switching of the fluid flow between the tubes. Some existing multi-path valves use a plurality of ball valves to control the direction of the fluid flow path within the system of tubes. While the existing multi-path valves control the passage of fluid through the system of tubes, the operation of the ball valves is performed directly inside the tubes with the ball valves contacting the fluid, thereby creating a potential for contamination.

Other existing multi-path valves can use a plurality of magnets to clamp tubes in a system of tubes from the outside. The magnets are only useful with small diameter flexible silicon tubes due to the small clamping force produced. Further, the small diameter flexible silicon tubes can only withstand low hydraulic pressure of the fluid.

SUMMARY OF THE INVENTION

Embodiments of the disclosure may provide a control valve. The control valve may include a tube housing, a tube within the tube housing that may be flexible, and a clamp within the tube housing. The tube may be disposed between a first portion of the tube housing and the clamp, and the clamp may be movable between an open position and a closed position. The clamp in the open position may be located away from the first portion of the tube housing such that the tube remains open, and the clamp in the first closed position may be located adjacent to the first portion of the tube housing such that the tube is clamped shut.

Embodiments of the disclosure may further provide a multi-path control valve. The multi-path control valve may include a tube housing, a tube that may be flexible, and a clamp. The flexible tube may have a first tube branch and a second tube branch, and the first tube branch and the second tube branch may be disposed within the tube housing. The clamp may also be disposed within the tube housing. The first tube branch may be disposed between a first portion of the tube housing and the clamp, and the second tube branch may be disposed between a second portion of the tube housing and the clamp. The clamp may be movable between an open position, a first closed position, and a second closed position. The open position may be a position in which the clamp is located away from the first portion and the second portion of the tube housing such that the first tube branch and the second tube branch remain open. The first closed position may be a position in which the clamp is located adjacent to the first portion of the tube housing such that the first tube branch is clamped shut while the second tube branch remains open. The second closed position may be a position in which the clamp is located adjacent to the second portion of the tube housing such that the second tube branch is clamped shut while the first tube branch remains open.

Embodiments of the disclosure may also provide a method for controlling a fluid flow through a multi-path tube. The method may include flowing fluid through a flow path from a first tube branch of a tube to a second tube branch of the tube while a third tube branch of the tube is closed. The method may also include closing the flow path of the first tube branch of the tube and flowing another fluid from the second tube branch of the tube to the third tube branch of the tube.

DETAILED DESCRIPTION

In one aspect, embodiments disclosed herein generally relate to a control valve for controlling a fluid flow through a tube system having any number of pathways. In other aspects, embodiments disclosed herein relate to a method of controlling a fluid flow through a multi-path control valve.

Figure 1:
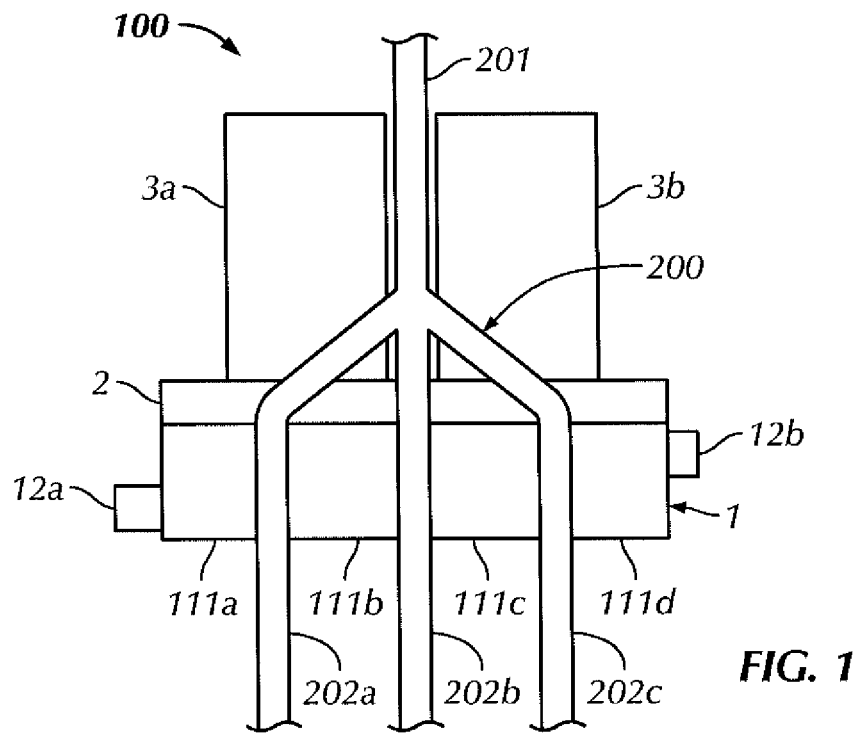
FIG. 1 is a bottom view of a multi-path control valve according to one or more embodiments of the present disclosure.
Figure 2:
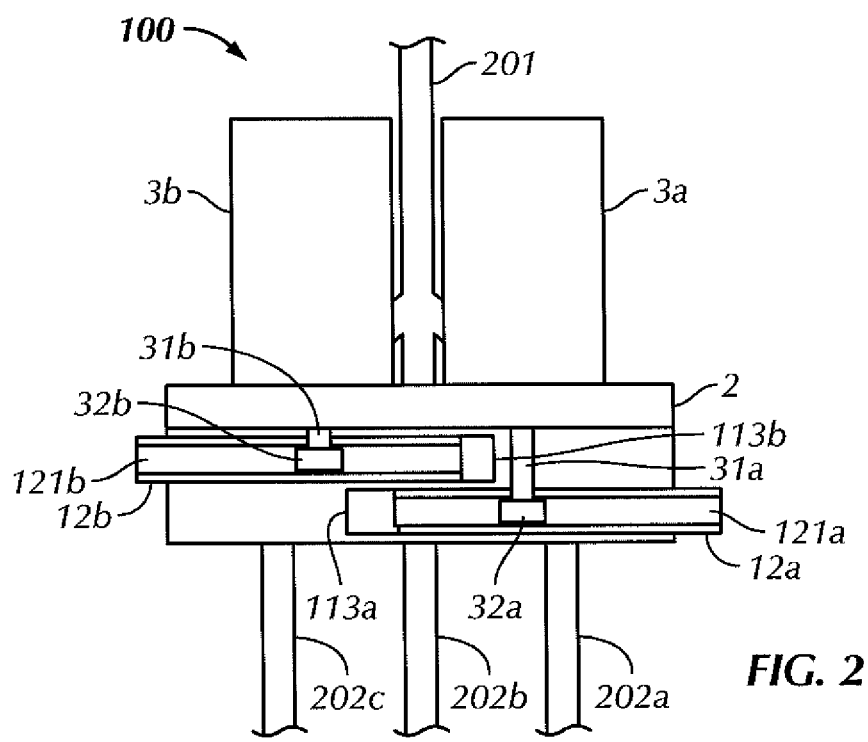
FIG. 2 is a top view of a multi-path control valve according to one or more embodiments of the present disclosure.

Referring to FIGS. 1 and 2, a bottom view and a top view of a multi-path control valve 100 according to one or more embodiments of the present disclosure are shown. In one or more embodiments, the multi-path control valve 100 may include a tube housing 1, a shaft housing 2, motors 3a, 3b, clamps 12a, 12b, shafts 31a, 31b, gears 32a, 32b and a multi-path tube 200. The multi-path control valve 100 may control fluid flow through the multi-path tube 200. Further, the multi-path tube 200 may include a main tube 201 and a plurality of tube branches 202a, 202b, 202c coupled to the main tube 201. The main tube 201, the first tube branch 202a, the second tube branch 202b, and the third tube branch 202c may be coupled together such that flow paths may be formed between each of the main tube 201, the first tube branch 202a, the second tube branch 202b, and the third tube branch 202c and the others of the main tube 201, the first tube branch 202a, the second tube branch 202b, and the third tube branch 202c. In one or more embodiments, the main tube 201, the first tube branch 202a, the second tube branch 202b, and the third tube branch 202c may be coupled together in any number of ways with any number of connection points between the main tube 201, the first tube branch 202a, the second tube branch 202b, and the third tube branch 202c. In other embodiments, the main tube 201 and the tube branches 202a, 202b, 202c may be coupled together at a single connection point. In other words, in one or more embodiments, a fluid flow path may be formed from the main tube 201 to any one the first tube branch 202a, the second tube branch 202b, or the third tube branch 202c. In other embodiments, a fluid flow path may be formed between any of the first tube branch 202a, the second tube branch 202b, and the third tube branch 202c via the main tube 201. In other words, in one or more embodiments, the main tube 201 may be closed off such that a fluid that enters the main tube 201 from one of the tube branches 202a, 202b, 202c and may exit by way of one of the tube branches 202a, 202b, 202c, which may be the same tube branch or a different tube branch from which the fluid entered.

In some embodiments, the multi-path tube 200 may be made of a flexible material such that flow paths may be closed by exerting a compressive force on the outer diameter of one or more tube branches of the multi-path tube. In one or more embodiments, the multi-path tube 200 may be made of silicon, polypropylene (PP), polyethylene (PE), polyurethane (PU), polyvinyl chloride (PVC), or any other flexible material known in the art.

Referring to FIGS. 1, 2, 3A, and 3B, in one or more embodiments, the tube branches 202a, 202b, 202c may each pass through the tube housing 1 such that portions of the first tube branch 202a, the second tube branch 202b, and the third tube branch 202c may be disposed within the tube housing 1. Multiple tube guide grooves 112a, 112b, 112c may be formed on a bottom surface of and within the tube housing 1, such that each tube branch 202a, 202b, 202c may be disposed within a separate tube guide groove 112a, 112b, 112c within the tube housing 1. In addition, the tube guide grooves 112a, 112b, 112c may separate the tube housing 1 into tube housing portions 111a, 111b, 111c, 111d.

Figure 3A:
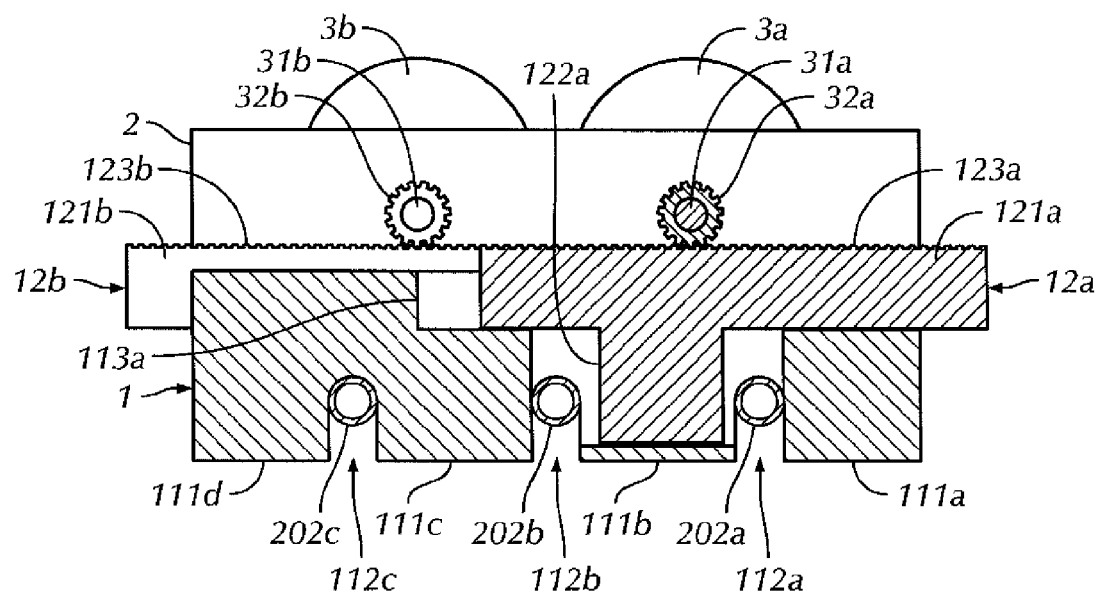
FIG. 3A is a cross-sectional view of a multi-path control valve through a lateral centerline of a first clamp guide groove in which a first clamp is disposed in an open position.
Figure 3B:
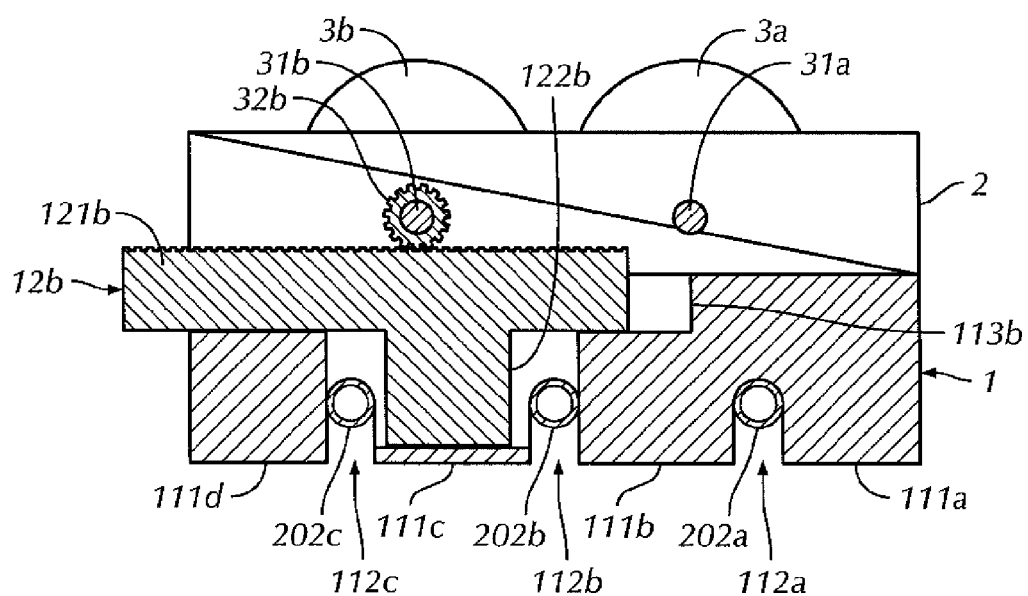
FIG. 3B is a cross-sectional view of a multi-path control valve through a lateral centerline of a second clamp guide groove in which a second clamp is disposed in an open position.

Further, in one or more embodiments, the first clamp 12a and the second clamp 12b may be disposed within clamp guide grooves 113a, 113b, respectively, within the tube housing 1. The clamp guide grooves 113a, 113b may be formed on a top surface of and within the tube housing 1 such that each clamp 12a, 12b may be disposed within a separate clamp guide groove 113a, 113b within the tube housing 1. Further, in one or more embodiments, the clamp guide grooves 113a, 113b may be formed such that the clamps 12a, 12b may shift in a direction that is substantially perpendicular to a longitudinal direction of the tube guide grooves 112a, 112b, 112c. Referring to FIGS. 3A and 3B, in one or more embodiments, each of the tube guide grooves 112a, 112b, 112c may pass through at least one of the clamp guide grooves 113a, 113b.

Referring to FIGS. 3A and 3B, in one or more embodiments, the first tube branch 202a may be disposed within the first tube guide groove 112a, which passes through the first clamp guide groove 113a, such that the first tube branch 202a is positioned between the first clamp 12a and the first portion 111a of the tube housing 1. Further, in one or more embodiments, the second tube branch 202b may be disposed within the second tube guide groove 112b, which passes through both the first clamp guide groove 113a and the second clamp guide groove 113b, such that the second tube branch 202b is positioned between the first clamp 12a and the third portion 111c of the tube housing 1 and between the second clamp 12b and the second portion 111b of the tube housing 1. Furthermore, in one or more embodiments, the third tube branch 202c may be disposed within the third tube guide groove 112c, which passes through the second clamp guide groove 113b, such that the third tube branch 202c is positioned between the second clamp 12b and the fourth portion 111d of the tube housing 1.

Referring to FIGS. 1, 2, 3A, and 3B, in one or more embodiments, clamps 12a, 12b may include a rack portion 121a, 121b and a clamp portion 122a, 122b. In one or more embodiments, each clamp portion 122a, 122b may be oriented perpendicularly relative to the respective rack portion 121a, 121b such that the respective clamp 12a, 12b may be substantially "T" shaped. Further, the clamp portion 122a of the first clamp 12a may protrude from the rack portion 121a into the first clamp guide groove 113a such that the first tube guide groove 112a, and thus, the first tube branch 202a is disposed between the clamp portion 122a of the first clamp 12a and the first portion 111a of the tube housing 1 and such that the second tube guide groove 112b, and thus, the tube branch 202b is disposed between the clamp portion 122a of the first clamp 12a and the third portion 111c of the tube housing 1. Furthermore, the clamp portion 122b of the second clamp 12b may protrude from the rack portion 121b into the second clamp guide groove 113b such that the second tube guide groove 112b, and thus, the tube branch 202b is disposed between the clamp portion 122b of the second clamp 12b and the second portion 111b of the tube housing 1 and such that the third tube guide groove 112c, and thus, the tube branch 202c is disposed between the clamp portion 122b of the second clamp 12b and the fourth portion 111d of the tube housing 1. In other embodiments, the clamp portion 122a, 122b does not need to be perpendicularly oriented relative to the respective rack portion 121a, 121b, and the clamp portion 122a, 122b may protrude from the respective rack portion 122a, 122b in any direction that positions the tube branches 202a, 202b, 202c between the clamp portions 122a, 122b and the portions 111a, 111b, 111c, 111d of the tube housing 1 and allows for the clamping of the tube branches 202a, 202b, 202c.

Additionally, in one or more embodiments, each rack portion 121a, 121b may have teeth 123a, 123b on a top surface. Further, in one or more embodiments, the gears 32a, 32b may engage the teeth 123a, 123b of the rack portions 121a, 121b, respectively, such that rotating one of the gears 32a, 32b will shift the respective clamp 12a, 12b laterally within the respective clamp guide grooves 113a, 113b. Furthermore, in one or more embodiments, the gears 32a, 32b may be coupled to shafts 31a, 31b, respectively. In one or more embodiments, the first gear 32a may be coupled to an end of a first shaft 31a such that the first gear 32a is maintained in contact with the rack portion 121a of the first clamp 12a. Further, in one or more embodiments, the second gear 32b may be coupled to an end of a second shaft 31b such that the second gear 32b is maintained in contact with the rack portion 121b of the second clamp 12b. In addition, the shafts 31a, 31b may be coupled to the gears 32a, 32b such that when one of the shafts 31a, 31b are rotated through an angle of rotation, the respective gear 32a, 32b rotates through the same angle of rotation as the shaft 31a, 31b. Further, the first shaft 31a and the second shaft 31b may pass through a shaft housing 2, and the shaft housing 2 may be coupled to a side of the tube housing 1 from which the tube branches 202a, 202b, 202c extend.

In one or more embodiments, the first clamp 12a may shift laterally between an open position, a first closed position, and a second closed position within the clamp guide groove 113a. Further, in one or more embodiments, the second clamp 12b may shift laterally between an open position, a first closed position, and a second closed position within the clamp guide groove 113b.

In one or more embodiments, as shown in FIG. 3A, the open position of the first clamp 12a may be a position in which the clamp portion 122a of the first clamp 12a is located between the first portion 111a and the third portion 111c of the tube housing 1 such that the flow path of the first tube branch 202a and the flow path of the second tube branch 202b remain open. Further, in one or more embodiments, the first closed position of the first clamp 12a may be a position in which the clamp portion 122a of the first clamp 12a is located adjacent to the first portion 111a of the tube housing 1 such that the flow path of the first tube branch 202a is closed between the clamp portion 122a of the first clamp 12a and the first portion 111a of the tube housing 1 and the flow path of the second tube branch 202b remains open. Furthermore, in one or more embodiments, the second closed position of the first clamp 12a may be a position in which the clamp portion 122a of the first clamp 12a is located adjacent to the third portion 111c of the tube housing 1 such that the flow path of the first tube branch 202a remains open and the flow path of the second tube branch 202b is closed between the clamp portion 122a of the first clamp 12a and the third portion 111c of the tube housing 1.

Additionally, in one or more embodiments, as shown in FIG. 3B, the open position of the second clamp 12b may be a position in which the clamp portion 122b of the second clamp 12b is located between the second portion 111b and the fourth portion 111d of the tube housing 1 such that the flow path of the second tube branch 202b and the flow path of the third tube branch 202c remain open. Further, in one or more embodiments, the first closed position of the second clamp 12b may be a position in which the clamp portion 122b of the second clamp 12b is located adjacent to the second portion 111b of the tube housing 1 such that the flow path of the second tube branch 202b is closed between the clamp portion 122b of the second clamp 12b and the second portion 111b of the tube housing 1 and the flow path of the third tube branch 202c remains open. Furthermore, in one or more embodiments, the second closed position of the second clamp 12b may be a position in which the clamp portion 122b of the second clamp 12h is located adjacent to the fourth portion 111d of the tube housing 1 such that the flow path of the second tube branch 202b remains open and the flow path of the third tube branch 202c is closed between the clamp portion 122b of the second clamp 12b and the fourth portion 111d of the tube housing 1.

In one or more embodiments, the shafts 31a, 31b may be coupled to motors 3a, 3b, respectively. The motors 3a, 3b may drive the shafts 31a, 31b in order to rotate the gears 32a, 32b and laterally shift the clamps 12a, 12b within the clamp guide grooves 113a, 113b, respectively. The motors 3a, 3b may constantly apply forces that may maintain the clamps 12a, 12b in the respective first closed position or second closed position when fluid pressure within the flow paths of the tube branches 202a, 202b, 202c pushes the clamps 12a, 12b towards the respective open position. In one or more embodiments, the motors 3a, 3b may be directly connected to the shaft housing 2. In one or more embodiments, the motors 3a, 3b may be servomotors. However, motors 3a, 3b are not necessary, and other powered actuators known in the art or human power may be used to shift and maintain the positions of the clamps 12a, 12b.

Figure 4A:
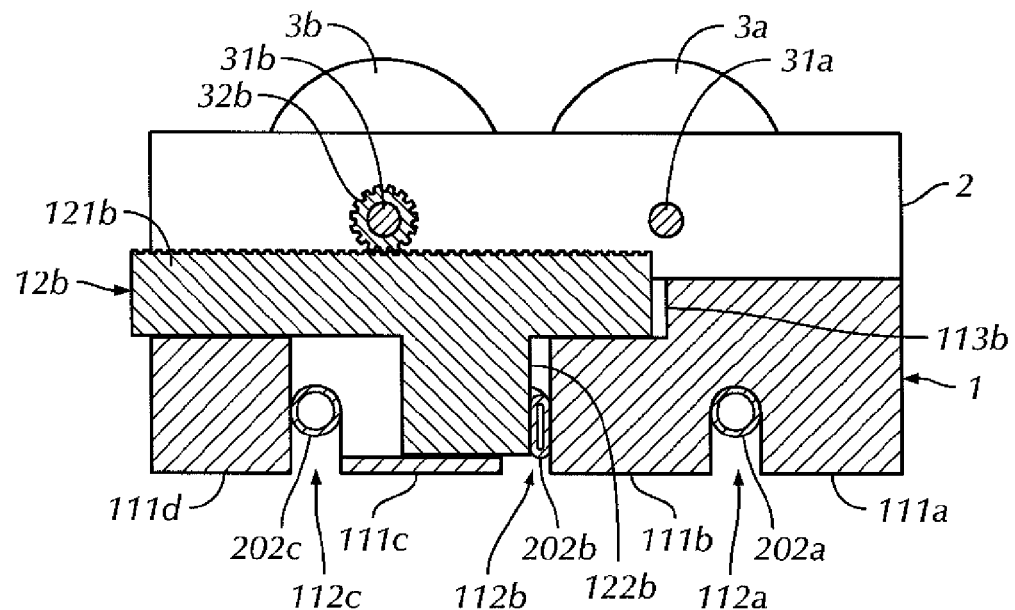
FIG. 4A is a cross-sectional view of a multi-path control through a lateral centerline of a second clamp guide groove in which a second clamp is disposed in a first closed position.
Figure 4B:
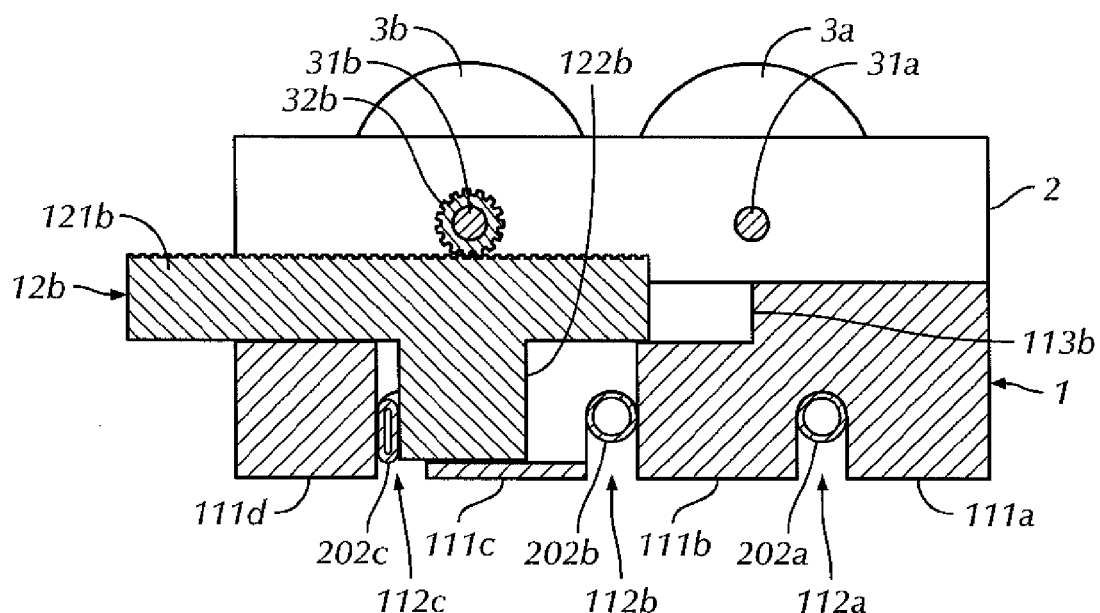
FIG. 4B is a cross-sectional view of a multi-path control through a lateral centerline of a second clamp guide groove in which a second clamp is disposed in a second closed position.

Since the first clamp 12a and the second clamp 12b are similar in function and structure, the first closed position of the second clamp 12b and the second closed position of the second clamp 12b are described in detail below and one of ordinary skill in the art will understand the first closed position of the first clamp 12a and the second closed position of the first clamp 12a. In one or more embodiments, the second clamp 12b may be located in a first closed position as shown in FIG. 4A. The first closed position of the second clamp 12b may be a position in which the clamp portion 122b of the second clamp 12b is located adjacent to the second portion 111b of the tube housing 1 and the flow path of the second tube branch 202b is closed between the clamp portion 122b of the second clamp 12b and the second portion 111b of the tube housing 1, while the flow path of the third tube branch 202c remains open. Further, in one or more embodiments, the second clamp 12b may be located in a second closed position as shown in FIG. 4B. A second closed position of the second clamp 12b may be a position in which the second clamp 12b is located adjacent to the fourth portion 111d of the tube housing 1 and the flow path of the third tube branch 202c is closed between the clamp portion 122b of the second clamp 12b and the fourth portion 111d of the tube housing 1, while the flow path of the second tube branch 202b remains open.

In one or more embodiments, the first clamp 12a may act separately from the second clamp 12b. Therefore, in one or more embodiments, any combination of the open position, the first closed position, or the second closed position of the first clamp 12a and the open position, the first closed position, or the second closed position of the second clamp 12b is possible. Further, as discussed above, motors 3a, 3b may be coupled to the shafts 31a, 31b, respectively, in order to drive the rotation of the shafts 31a, 31b, which rotates the gears 32a, 32b, respectively, which laterally shifts the clamps 12a, 12b, respectively, within the respective clamp guide grooves 113a, 113b. Therefore, the motors 3a, 3b may shift the clamps 12a, 12b, respectively, between the clamps 12a, 12b respective open positions, first closed positions, and second closed positions. Further, the motors 3a, 3b may maintain the clamps 12a, 12b in the respective first closed position or second closed position when fluid pressure within a flow path of the tube branches 202a, 202b, 202c pushes the clamps 12a, 12b towards the respective open positions. In one or more embodiments, the motors 3a, 3b may be directly connected to the shaft housing 2. However, motors 3a, 3b are not necessary, and other powered actuators known in the art or human power may be used to rotate the shafts 31a, 31b to shift the clamps 12a, 12b and to maintain the positions of the clamps 12a, 12b against fluid pressure within the flow paths of the tube branches 202a, 202b, 202c. Further, in one or more embodiments, one or more powered actuators may rotate the shafts 31a, 31b to shift the clamps 12a, 12b in unison.

Additionally, one skilled in the art could envision a system having a single tube in place of the multi-path tube, using a single clamp to close the flow path of the single tube. Further, in one or more embodiments, a multi-path tube may have two tube branches and one clamp may be used to close a flow path until only a single flow path of the multi-path tube remains open. Additionally, in one or more embodiments, a multi-path tube may have two tube branches and two clamps may be used to close both flow paths. Furthermore, in one or more embodiments, a multi-path tube may have more than three tube branches ('a' tube branches), in which case, more clamps ('a-1' clamps) would be required to maintain the ability to close flow paths of tube branches until only a single flow path of the multi-path tube remains open. Moreover, a multi-path tube having any number of branches ('b' tube branches) may have an equal number of clamps ('b' clamps) such that all flow paths of the tube branches of the multi-path tube may be closed. In addition, a multi-path control valve 100, as described above, may be used with a multi-path tube 200 of any diameter. Further, in one or more embodiments, at least the tube housing 1, the shaft housing 2, the first clamp 12a, and the second clamp 12b may be made of metal (e.g., steel), plastic, metal reinforced epoxy, or any other material stronger than the material used for the multi-path tube 200.

In one example, a multi-path control valve, as discussed above and shown in FIGS. 1, 2, 3A, and 3B, may be used to perform dialysis. In the example, the multi-path tube 200 is made of PVC and has a diameter of approximately 6 centimeters. Further, the tube housing 1, the shaft housing 2, the first clamp 12a, and the second clamp 12b are made of steel, and the motors 3a, 3b are servomotors. The first tube branch 202a may be connected to a fluid source, the second tube branch 202b may be disposed within a patient, the third tube branch 202c may be connected to a waste disposal container, and the main tube 201 may be closed off. Referring to FIGS. 3A and 3B, the first clamp 12a and the second clamp 12b may each be disposed in the respective open positions.

Dialysis may include providing a fluid to the patient in order to extract waste. In the example, the fluid provided to the patient is dialysate. A waste fluid is then removed from the patient and disposed in the waste disposal container. The waste fluid being made up of dialysate and blood containing waste material. A cleaning fluid is then pumped through all tubing in order to clean out any remnant waste left behind during disposal.

To provide a fluid to the patient, the third tube branch 202c is closed off and a fluid flow path is maintained between the first tube branch 202a and the second tube branch 202b. In order to close the third tube branch 202e, the second motor 3b is activated in order to rotate the second shaft 31b in a clockwise direction, which rotates the second gear 32b in a clockwise direction. The rotation of the second gear 32b in a clockwise direction shifts the second clamp 12b laterally from the open position of the second clamp 12b towards a second closed position of the second clamp 12b. The second clamp 12b shifts until the clamp portion 122b of the second clamp 12b is located adjacent to the fourth portion 111d of the tube housing 1, which is the second closed position of the second clamp 12b, and a flow path through the third tube branch 202c is closed. Once the third tube branch 202c is closed, a first fluid flows from the fluid source into the patient via the first tube branch 202a and the second tube branch 202b. In one or more embodiments, the first fluid may be a dialysis fluid.

To dispose of a second fluid from the patient, the first tube branch 202a is closed off and the third tube branch 202c is opened to create a fluid flow path between the second tube branch 202b and the third tube branch 202c. To close off the first tube branch 202a, the first motor 3a is activated in order to rotate the first shaft 31a in a counterclockwise direction, which rotates the first gear 32a in a counterclockwise direction. The rotation of the first gear 32a in a counterclockwise direction shifts the first clamp 12a laterally from the open position of the first clamp 12a towards a first closed position of the first clamp 12a. The first clamp 12a shifts until the clamp portion 122a of the first clamp 12a is located adjacent to the first portion 111a of the tube housing 1, which is the first closed position of the first clamp 12a, and a flow path through the first tube branch 202a is closed. Once the first tube branch 202a is closed, all three tube branches 202a, 202b, 202c are isolated from each other.

Afterwards, to open the third tube branch 202c, the second motor 3b is activated in order to rotate the second shaft 31b in a counterclockwise direction, which rotates the second gear 32b in a counterclockwise direction. The rotation of the second gear 32b in a counterclockwise direction shifts the second clamp 12b laterally from the second closed position of the second clamp 12b towards the open position of the second clamp 12b. The second clamp 12b shifts until the clamp portion 122b of the second clamp 12b is located between the second portion 111b and the fourth portion 111d of the tube housing 1, which is the open position of the second clamp 12b, and a flow path through the second tube branch 202b and the flow path through the third tube branch 202c are open. Once the third tube branch 202c is opened, a second fluid flows from the patient into the waste disposal container via the second tube branch 202b and the third tube branch 202c. In one or more embodiments, the second fluid may be a waste fluid.

Once the second fluid is removed from the patient and discarded into the waste disposal container, the second tube branch 202b may be removed from the patient and connected to the waste disposal container. Next, to flow a third fluid through each of the tube branches 202a, 202b, 202c in order to clean out any excess of the first fluid and the second fluid, the first tube branch 202a is opened. To open the first tube branch 202a, the first motor 3a is activated in order to rotate the first shaft 31a in a clockwise direction, which rotates the first gear 32a in a clockwise direction. The rotation of the first gear 32a in a clockwise direction shifts the second clamp laterally from the first closed position of the first clamp 12a towards the open position of the first clamp 12a. The first clamp 12a shifts until the clamp portion 122a of the first clamp 12a is located between the first portion 111a and the third portion 111c of the tube housing 1, which is the open position of the first clamp 12a, and the flow path through the first tube branch 202a and the flow path through the second tube branch 202b are open. Once the first tube branch 202a is opened, a third fluid flows through the second tube branch 202b and the third tube branch 202c in order to clean out the first fluid and the second fluid previously flowed through the multi-path tube 200. In one or more embodiments, the third fluid may be a cleaning fluid.

In order to aid in cleaning, the second clamp 12b may be shifted into one of the first closed position of the second clamp 12b and the second closed position of the second clamp 12b. Closing one of the second tube branch 202b and the third tube branch 202c allows for flow of the cleaning fluid to be isolated within the other one of the second tube branch 202b and the third tube branch 202c and more easily clean the other of the second tube branch 202b and the third tube branch 202c.

In other examples, a multi-path control valve may be used for waste water treatment, for water purification, in a chemical reactor, in a fluid system of a body, in a distillation facility, or any other system relating to fluid flow.

While the disclosure includes a limited number of embodiments, those skilled in the art, having benefit of this disclosure, will appreciate that other embodiments may be devised which do not depart from the scope of the present disclosure. Accordingly, the scope should be limited only by the attached claims.

What is claimed is:
1. A multi-path control valve comprising:
a tube housing;
a tube having a first tube branch and a second tube branch, the first tube branch and the second tube branch disposed through the tube housing;
a first clamp disposed within the tube housing,
wherein the first tube branch is disposed between a first portion of the tube housing and the first clamp, wherein the second tube branch is disposed between a second portion of the tube housing and the first clamp,
wherein the first clamp is movable between an open position, a first closed position, and a second closed position,
wherein the first clamp in the open position is located away from the first portion and the second portion of the tube housing,
wherein the first clamp in the first closed position is located adjacent to the first portion of the tube housing and away from the second portion of the tube housing, and
wherein the first clamp in the second closed position is located adjacent to the second portion of the tube housing and away from the first portion of the tube housing;
a second clamp disposed within the tube housing,
wherein the tube further comprises a third tube branch, the third tube branch disposed through the tube housing,
wherein the second tube branch is disposed between a third portion of the tube housing and the second clamp,
wherein the third tube branch is disposed between a fourth portion of the tube housing and the second clamp,
wherein the second clamp is movable between an open position, a first closed position, and a second closed position,
wherein the second clamp in the open position is located away from the third portion and the fourth portion of the tube housing,
wherein the second clamp in the first closed position is located adjacent to the third portion of the tube housing and away from the fourth portion of the tube housing, and
wherein the second clamp in the second closed position is located adjacent to the fourth portion of the tube housing and away from the third portion of the tube housing;
a first tube groove, a second tube groove, and a third tube groove formed on a bottom surface of the tube housing,
wherein the first tube branch is disposed within the first tube groove, the second tube branch is disposed within the second tube groove, and the third tube branch is disposed within the third tube groove; and
a first clamp groove and a second clamp groove formed on a top surface of the tube housing,
wherein the first clamp is disposed within the first clamp groove, and
wherein the second clamp is disposed within the second clamp groove.

2. The multi-path control valve of claim 1, wherein the tube is flexible.

3. The multi-path control valve of claim 1, wherein:
the first tube groove and the second tube groove travel through the first clamp groove; and
the second tube groove and the third tube groove travel through the second clamp groove.

4. A multi-path control valve comprising:
a tube housing;
a tube having a first tube branch and a second tube branch, the first tube branch and the second tube branch disposed through the tube housing;
a first clamp disposed within the tube housing,
wherein the first tube branch is disposed between a first portion of the tube housing and the first clamp,
wherein the second tube branch is disposed between a second portion of the tube housing and the first clamp,
wherein the first clamp is movable between an open position, a first closed position, and a second closed position,
wherein the first clamp in the open position is located away from the first portion and the second portion of the tube housing,
wherein the first clamp in the first closed position is located adjacent to the first portion of the tube housing and away from the second portion of the tube housing, and
wherein the first clamp in the second closed position is located adjacent to the second portion of the tube housing and away from the first portion of the tube housing,
a second clamp disposed within the tube housing, wherein:
the tube further comprises a third tube branch, the third tube branch disposed through the tube housing;
the second tube branch is disposed between a third portion of the tube housing and the second clamp;
the third tube branch is disposed between a fourth portion of the tube housing and the second clamp;
the second clamp is movable between an open position, a first closed position, and a second closed position;
the second clamp in the open position is located away from the third portion and the fourth portion of the tube housing;
the second clamp in the first closed position is located adjacent to the third portion of the tube housing and away from the fourth portion of the tube housing;
the second clamp in the second closed position is located adjacent to the fourth portion of the tube housing and away from the third portion of the tube housing
a shaft housing coupled to the tube housing,
a first shaft coupled to the shaft housing;
a second shaft coupled to the shaft housing;
a first gear coupled to an end of the first shaft such that rotating the first shaft rotates the first gear, and wherein the first gear is coupled to the first clamp such that rotating the first gear laterally shifts the first clamp; and
a second gear coupled to an end of the second shaft such that rotating the second shaft rotates the second gear, and wherein the second gear is coupled to the second clamp such that rotating the second gear laterally shifts the second clamp.

5. The multi-path control valve of claim 4, further comprising:
a first motor connected to the shaft housing and coupled to the first shaft such that the first motor controls a rotation of the first shaft; and
a second motor connected to the shaft housing and coupled to the second shaft such that the second motor controls a rotation of the second shaft.

6. A multi-path control valve comprising:
a tube housing;
a tube having a first tube branch and a second tube branch, the first tube branch and the second tube branch disposed through the tube housing;
a first clamp disposed within the tube housing,
wherein the first tube branch is disposed between a first portion of the tube housing and the first clamp, wherein the second tube branch is disposed between a second portion of the tube housing and the first clamp, and wherein the first clamp is movable between an open position, a first closed position, and a second closed position, wherein the first clamp in the open position is located away from the first portion and the second portion of the tube housing, wherein the first clamp in the first closed position is located adjacent to the first portion of the tube housing and away from the second portion of the tube housing, and wherein the first clamp in the second closed position is located adjacent to the second portion of the tube housing and away from the first portion of the tube housing, the first clamp further comprising a first rack portion coupled to a first gear, and a first clamping portion that protrudes from the first rack portion of the first clamp such that the first tube branch is disposed between the first clamping portion of the first clamp and the first portion of the tube housing and the second tube branch is disposed between the first clamping portion of the first clamp and the second portion of the tube housing;

a second clamp disposed within the tube housing, wherein:

the tube further comprises a third tube branch, the third tube branch disposed through the tube housing;

the second tube branch is disposed between a third portion of the tube housing and the second clamp;

the third tube branch is disposed between a fourth portion of the tube housing and the second clamp;

the second clamp is movable between an open position, a first closed position, and a second closed position;

the second clamp in the open position is located away from the third portion and the fourth portion of the tube housing;

the second clamp in the first closed position is located adjacent to the third portion of the tube housing and away from the fourth portion of the tube housing; and the second clamp in the second closed position is located adjacent to the fourth portion of the tube housing and away from the third portion of the tube housing;

the second clamp further comprising a second rack portion coupled to a second gear; and a second clamping portion that protrudes from the second rack portion of the second clamp such that the second tube branch is disposed between the second clamping portion of the second clamp and the third portion of the tube housing and the third tube branch is disposed between the second clamping portion of the second clamp and the fourth portion of the tube housing.

\* \* \* \* \*